United States Patent [19]

Toyota et al.

[11] Patent Number: 4,625,714
[45] Date of Patent: Dec. 2, 1986

[54] ENDOSCOPE HAVING A CONTROL FOR IMAGE STAND STILL AND PHOTOGRAPHING THE IMAGE

[75] Inventors: Makoto Toyota; Fumitaka Takeshita; Satoshi Arakawa, all of Omiya, Japan

[73] Assignee: Fuji Photo Optical Co., Ltd., Saitama, Japan

[21] Appl. No.: 766,411

[22] Filed: Aug. 16, 1985

[30] Foreign Application Priority Data

Aug. 20, 1984 [JP] Japan ................. 59-172795

[51] Int. Cl.$^4$ .............................................. A61B 1/04
[52] U.S. Cl. .......................................... 128/6; 358/98
[58] Field of Search .......................... 128/4, 6; 358/98

[56] References Cited

U.S. PATENT DOCUMENTS 4,475,539  10/1984  Konomura ............................. 128/6

Primary Examiner—William H. Grieb
Attorney, Agent, or Firm—Parkhurst & Oliff

[57] ABSTRACT

An endoscope used for observing the interior of a cavity and the like of a living human body. The endoscope according to the present invention is of such an arrangement that an image sensor is provided in the forward end of an insertion section and an object of interest can be displayed on a screen of a television set in response to a video signal obtained from the image sensor. According to the present invention, a control unit is provided therein with a circuit for producing an image standstill command and a shutter release command depending on a time or times of operation, or a step or steps in press-in value of a single push in switch provided a control section of the endoscope, so that the provision of a single control button makes it possible to make a monitored image stand still and to release a shutter of a camera.

3 Claims, 6 Drawing Figures

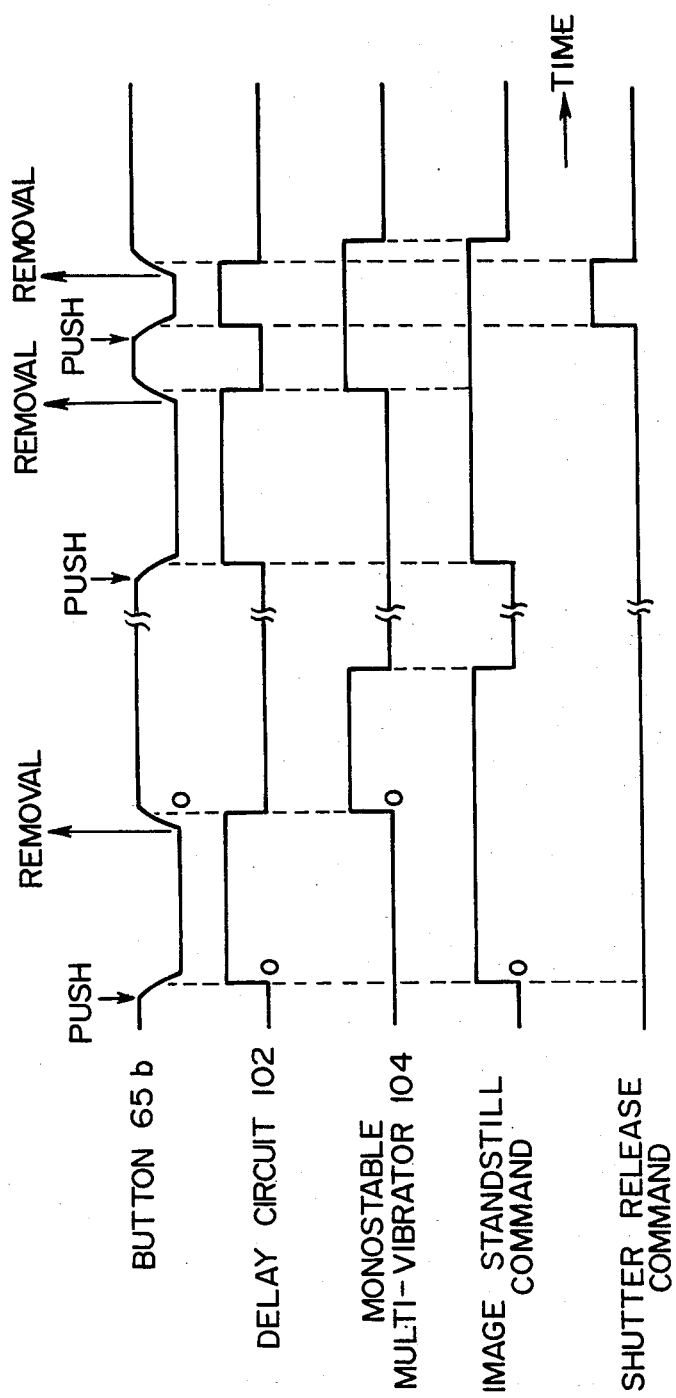

ENDOSCOPE HAVING A CONTROL FOR IMAGE STAND STILL AND PHOTOGRAPHING THE IMAGE

BACKGROUND OF THE INVENTION

1. Field of the Invention

The present invention relates to an endoscope utilizing a solid state imaging device, and more particularly to an endoscope wherein the standstill control of an image of a monitor television set and the shutter operation of a camera are effected by a single control button provided on a control section of the endoscope.

2. Description of the Prior Art

Recently, there has been proposed an endoscope of a novel type, wherein a solid state imaging device such as an image sensor of a charge coupled device (CCD) type or a metal oxide silicon (MOS) type is provided in the forward end of an insertion section of the endoscope, and a video signal of an object of interest obtained from this solid state imaging device is displayed on a screen of a monitor television set or the like through a control unit, so that the object of interest can be observed. In the above-described endoscope of the novel type, differing from a conventional endoscope which has been adapted to directly observe an image transmitted by an optical fiber bundle through an eyepiece section, the image of interest is observed on the screen of the television set and the like, so that such advantages can be offered that the eyepiece section can be dispensed with and the control section can be handled in an easy posture.

FIG. 1 shows an outline of the arrangement of the endoscope of this novel type.

In FIG. 1, designated at 10 is a generally pistol-shaped control section, 12 a control unit provided with various control mechanisms including a light source, and 14 a monitor television set. The control section is constituted by a grip portion 10A, a button 10B for suction and air-water supply and an angle control knob 10C. Connected to the forward portion of the control section 10 is an insertion section 16 operable in a very deep portion of a living body or the like. Connected to the bottom portion of the grip portion 10A of the control section 10 is one end of a connector section 18, the other end of which is bifurcated. A plug 20 and a connector 22 are provided on the bifurcated end portions, respectively. The plug 20 is provided with a light guide rod 24, a terminal pin for controlling a value for air and water supply, being interlocked with the control button 10B of the control section 10, a tube connected to an air supply pump in the control unit 12 and the like. The plug 20 is connected to a socket 26 of the control unit 12. Furthermore, the connector 22, being connected to a socket 28, outputs a driving signal from the control unit 12 to a solid state imaging device incorporated in the forward end of the insertion section 16 and inputs a video signal from the solid state imaging device to the control unit 12.

As shown in FIG. 2, the control unit 12 is constituted by:

a light quantity control section 32 for manually adjusting a quantity of light from a light source 30;

a rotary color filter 38 provided on a disc thereof with filters of three colors including R(red), G(green), and B(blue) and arranged at intervals of every 120° or 1/3n (n is an integer), having a function of successively changing a light from the light source 30 into colors including R, G and B and supplying the same to a light guide 34, and rotatably driven by a motor 36;

a video signal processing section 42 for feeding a driving signal S s to a solid state imaging device 40 in the forward end of the insertion section, synchronizing image pickup signals Sv from the solid state imaging device 40 with color changeover timings of the rotary color filter to obtain color sequential signals including R, G and B, and outputting separation signals including R, G and B;

a control section 44 for controlling a valve and the like interlocked with the control button 10B of the control section 10; and a power source section 46 for feeding electric power to the video signal processing section 42.

The video signal processing section 42 is constituted by:

an image processor 50 for delivering R, G and B image signals successively outputted from the solid state imaging device 40 in synchronism with the rotation of the motor 36, i.e. the rotation of the rotary color filter 32 to memories of respective color signals;

an analogue-digital (A/D) converter 52 for converting an analogue color signal outputted from the processor 50 into a digital color signal;

a R signal memory 54a, a G signal memory 54b and a B signal memory 54c for storing R, G and B signals successively outputted from the converter 52;

digital-analogue (D/A) converters 56a~56c connected to memories 54a~54c, for converting image signals outputted from the respective memories into analogue signals; and an output processor 58 for reading R, G and B signals outputted from these D/A converters 56a~56c, composing the same to provide a color image, converting the color image into NTSC (National television system committee) signals or signals or the like and outputting the same. Additionally, when a standstill signal SH is applied from a terminal 60 to the output processor 58, the output processor 58 stops the readout from the memories 54a~54c, prevents the write-in of buffer memories in the output processor 58, and repeatedly performs only the read-out, so that the image display on the monitor television set 14 can be stopped.

Furthermore, the production of monochromatic lights of R, G and B has been made by use of the filter 38, however, light sources producing three primary colors, respectively, may be used.

Description will hereunder be given of action of the endoscope with the above-described arrangement. In the first place, an operator inserts the plug 20 into the socket 26 of the control unit 12 and connector 22 into the socket 28 of the control unit. The operator turns on power source switches of the control unit 12 and the monitor television set 14, adjusts the lamp light quantity control section 32 (an adjusting knob is provided on a panel face of the control unit 12), and directs the lights of red, green and blue successively emitted from a lens provided on an emitting end of the light guide through the light guide inserted into the endoscope. Subsequently, the operator grasps the control section 10 and inserts the forward end of the insertion section 16 little by little to the position of the object of interest, watching the image displayed on the monitor television 14. After the forward end of the insertion section 16 is set at a desirable position, subsequently, the control knob 10c is rotated and the forward end portion of the insertion section is directed to the position of observation, while the monitor television set 14 is being observed. Furthermore, the control button 10B is operated by an index finger as necessary, to perform a water supply operation, an air supply operation or a suction operation. Further, when necessary, a forceps or the like is inserted through an insertion hole, not shown, of the control section 10, whereby a piece of flesh in an affected portion may be picked and so forth.

An image of an affected portion is picked up by the solid state imaging device 40 through a lens incorporated in the forward end portion of the insertion section 16, photoelectro-transducing signals thereof are successively outputted in the order R→G→B, and successively stored in the memories 54a~54c for exclusive uses by every color components through the image processor 50 and the A/D converter 52. Upon completion of storing of one picture, image data of three colors are read out of the memories 54a~54c through the D/A converters 56a~56c, and outputted to the output processor 58. The output processor 58 composes R, G and B signals to produce a color picture, further, applies a predetermined process thereto so that the picture can be seen on the ordinary monitor television set, and the picture is outputted.

Now, as the mode of use of the endoscope, there are many cases where the operator tries to grasp the conditions of an affected portion, while observing an image on the screen of the monitor television set, and the images frequently need to be recorded and preserved. As a measure of recording, the picture thus monitored is photographed by a still camera.

In this case, in order to photograph the image displayed on the monitor television set stably and clearly, it is desirable to make the monitored image stand still, and thereafter, to release the shutter of the camera. However, when the control section 10 of the endoscope is provided with two buttons for making the image stand still and for releasing the shutter of the camera, if photographing by use of the camera is performed, then the two buttons should be operated separately of each other, thus presenting the disadvantages that it is troublesome to operate the buttons separately of each other and quick operations cannot be performed.

SUMMARY OF THE INVENTION

The present invention has been developed to obviate the above-described disadvntages of the prior art and has as its object the provision of an endoscope wherein the provision of one button on the control section makes it possible to make the image stand still and to release the shutter of the camera, thus improving the controllability.

To this end, the present invention contemplates that the control unit is provided with a circuit for producing an image standstill command and a shutter release command depending on a time or times of operation, or a step or steps in press-in value of the switch provided on the endoscope.

BRIEF DESCRIPTION OF THE DRAWINGS

The exact nature of this invention, as well as other objects and advantages thereof, will be readily apparent from consideration of the following specification relating to the accompanying drawings, in which like reference characters designate the same or similar parts throughout the figures thereof and wherein:

FIG. 6 is an action time chart of respective portions in the circuit shown in FIG. 5.

DETAILED DESCRIPTION OF THE INVENTION

Detailed description will hereunder be given of the preferred embodiments of the endoscope according to the present invention with reference to the accompanying drawings.

Figure 1:
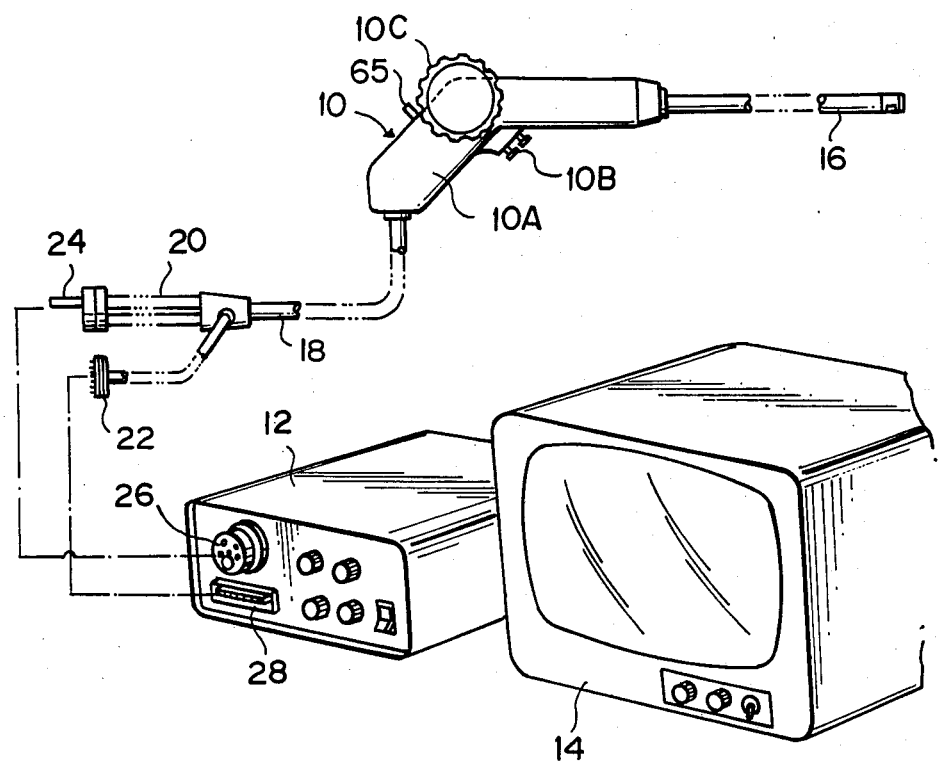
FIG. 1 is a block diagram showing one example of a television endoscope incorporating therein a solid state imaging device.
Figure 2:
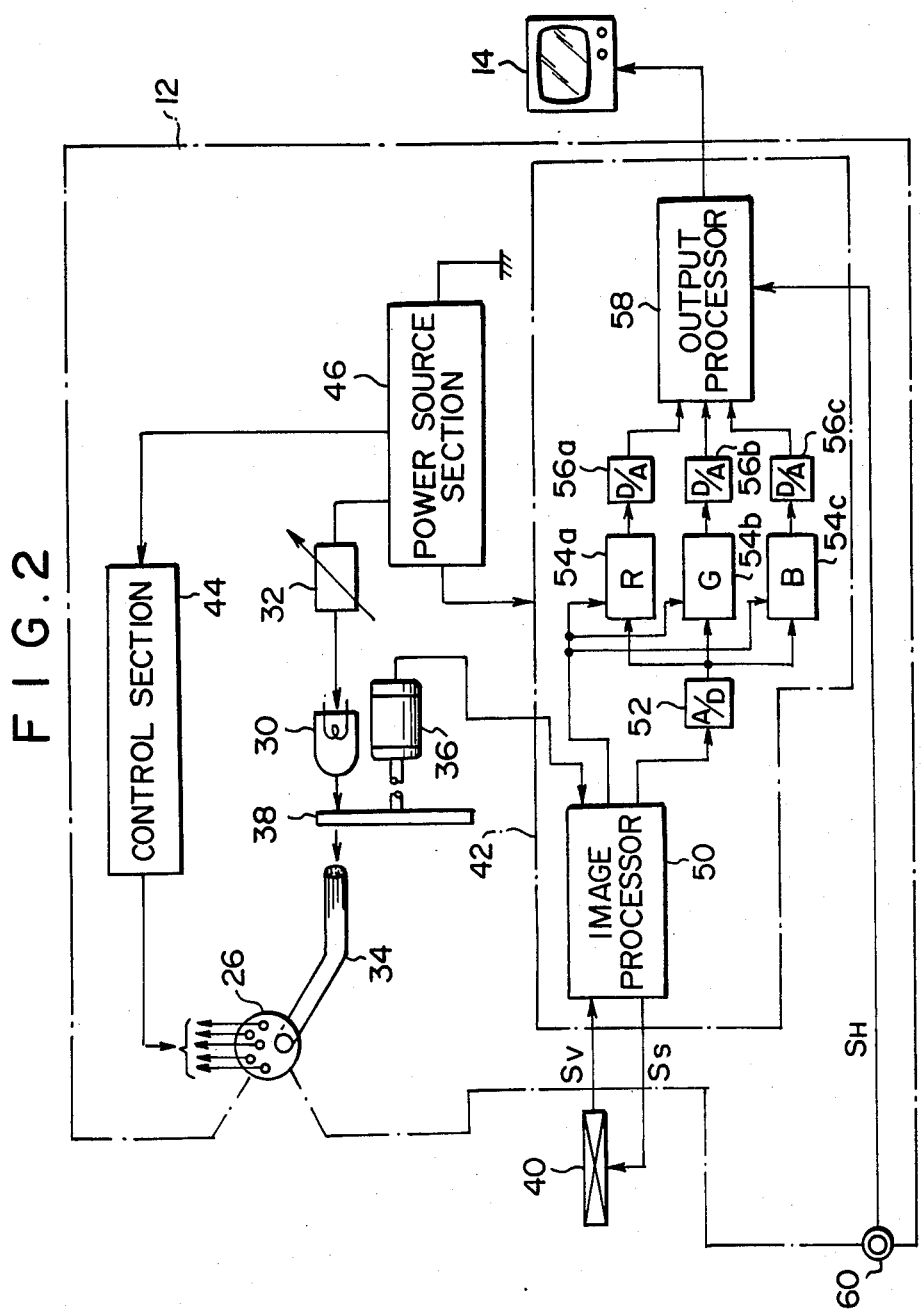
FIG. 2 is a block diagram showing the arrangement of the control unit of the television endoscope.
Figure 3:
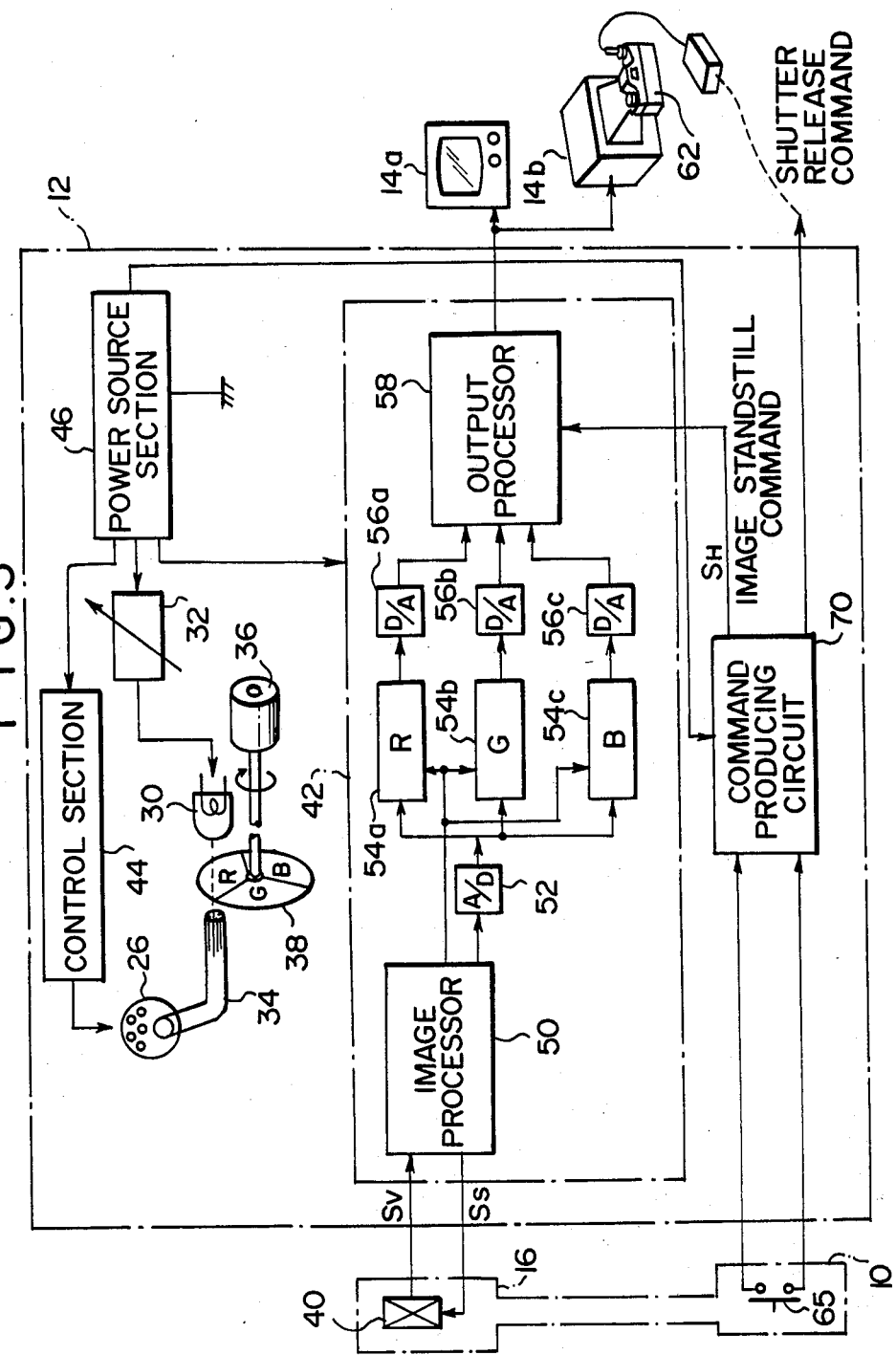
FIG. 3 is a block diagram showing one embodiment of the present invention.

FIG. 3 shows one embodiment of the present invention. In this embodiment, the portions or members corresponding to those shown in FIG. 2 are depicted by the same reference numerals as the latter to avoid doubled description. The present invention is different from those shown in FIGS. 1 and 2 in that the control section 10 of the endoscope is provided with a photographing button 65 and the control unit 12 is provided therein with a command producing circuit 70 interlocked with the opration of the photographing button 65 to produce a command SH for making an image stand still and a command for releasing the shutter of the camera. In general, in photographing by use of a camera, there are provided a monitor television set 14a for allowing the operator to observe and another monitor television set 14b to which is set a camera 62 exclusively used for photographing, and both the monitor television sets are connected to the output processor 58, respectively.

Figure 4:
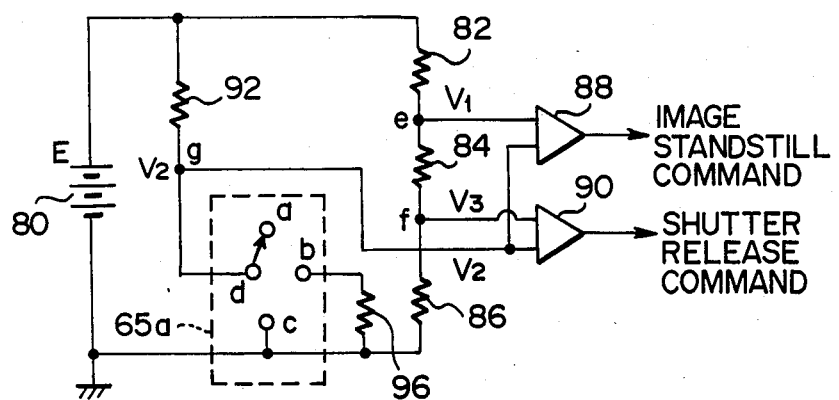
FIGS. 4 and 5 are circuit diagrams showing a first and a second embodiments of a command producing circuit 70 according to the present invention.

FIG. 4 is a circuit diagram showing one embodiment of the command producing circuit 70.

Three resistors 82, 84 and 86, which have resistance values equal to one another, are connected in series to opposite ends of a direct current power source 80, a connecting point e between the resistors 82 and 84 is connected to one of input terminals of a comparator 88, and a connecting point f between the resistors 84 and 86 is connected to one of input terminals of a comparator 90. The other of input terminals of the comparator 88 and the other of input terminals of the comparator 90 are connected to each other, and a resistor 92 is inserted between these and the end of the resistor 82 on the power source's side. Furthermore, inserted between an output end of the resistor 92 and an earth line is a series circuit including a push button switch 65a of two step actions and a resistor 96 having a resistance value equal to the resistance 92. The push button switch 65a includes three stationary contact points a, b and c, the resistor 96 is inserted between the contact point b and the earth, and the contact point c is directly earthed. Furthermore, a movable contact point d of the push button switch 65a is connected to an output end of the resistor 92.

With the above-described arrangement, when the push button switch 65a is not operated, the movable contact point d is connected to the stationary contact point a, a voltage V2 at a connecting point g between the resistor 92 and the movable contact point d is E, a voltage V1 at the connecting point e is 2E/3, and a voltage V3 at the connecting point f is 1E/3. In this case, the comparator 88 has a relationship of $V1<V2$, and the comparator 90 has a relationship of $V2>V3$. When $V1>V2$, the comparator 88 produces an output signal, and, when $V2<V3$, the comparator 90 produces an output signal, In consequence, in this stage, neither image standstill command nor shutter release command is outputted.

When the push button switch 65a is pushed in to half way, the movable contact point d comes into contact with the stationary contact point b. As the result, the voltage V2 at the connecting point g becomes E/2, which is lower than the voltage V1 at the connecting point e, whereby the comparator 88 is operated and an output signal is produced as the image standstill command SH. In this case, even if V2 is lowered, since the comparator 90 has the relationship of $V2>V3$, no output signal is produced.

Further, when the push button 65a is pushed in deeper, the movable contact point d comes into contact with the stationary contact point c. As the result, the voltage V2 at the connecting point g becomes zero and V2 becomes lower than V3, whereby, in the comparator 90, an output signal is produced as the shutter release command. In this case, since the relationship of $V1>V2$ of the comparator 88 is still maintained, the image standstill command is continuously outputted. The shutter release command drives an electromagnetic solenoid, not shown, whereby the shutter button of the camera 62 is driven. When the finger is removed from the push button switch 65a, both the comparators 90 and 88 are successively returned to the initial states and the two commands disappear.

Figure 5:
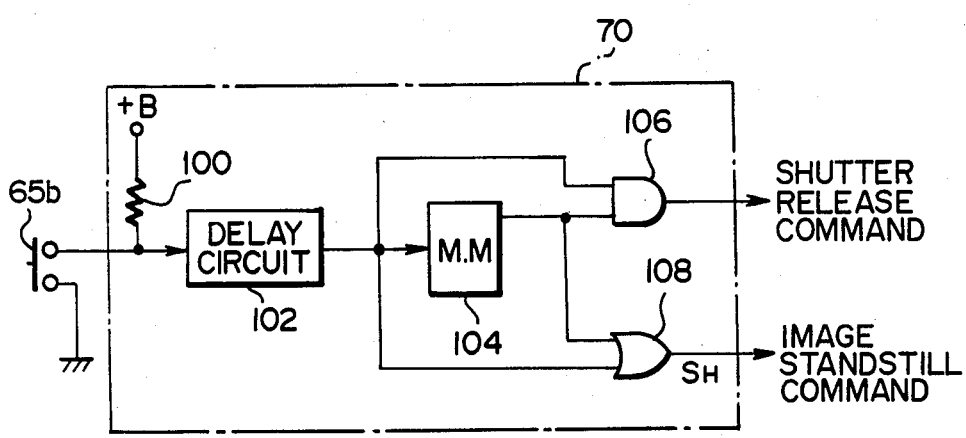

FIG. 5 is a circuit diagram showing another embodiment of the command producing circuit 70.

In this embodiment, as a command producing button switch 65, there is used a non-lock type push button switch 65b of one action. Connected to one of terminals of the push button switch 65b is a resistor 100 connected to a power source (+B), and the other of terminals thereof is earthed. One end of the push button switch 65b is connected to a delay circuit 102, whereby an output signal is produced by the delay circuit 102 a predetermined time duration after the push button switch 65b is pushed. Connected to an output terminal of the delay circuit 102 are an AND gate 106 and an OR gate 108 in addition to a monostable multi-vibrator (M,M) 104. When the output signal of the delay circuit 102 falls, the monostable multi-vibrator 104 outputs a signal of "H" level for a time duration determined by a preset time constant. An output terminal of the monostable multi-vibrator 104 is connected to the other input terminals of the AND gate 106 and the OR gate 108.

Description will now be given of action in the above-described arrangement with reference to the time chart shown in FIG. 6.

When the push button switch 65b is pushed in, the end of the resistor 100 on the output side is earthed, and the input terminal of the delay circuit 102 comes to be on zero level, whereby a signal on "H" level is produced after a predetermined time duration. Since this output signal from the delay circuit 102 is applied to the OR gate 108, whereby a signal on "H" level is produced at the output terminal of the OR gate 108, which becomes the image standstill command SH. This image standstill command SH is continously produced while the push button switch 65b is pressed. When the finger is removed from the push button switch 65b, the output signal from the delay circuit 102 is returned to the "L" level under some hysteresis. In synchronism with the fall of this wave form, an output signal on "H" level is produced from the monostable multi-vibrator 104. Since this output signal from the monostable multi-vibrator 104 is applied to the OR gate 108, even if the output signal from the delay circuit 102 is returned to the "L" leve, the image standstill command is produced without being interrupted. On the other hand, the output signal from the monostable multi-vibrator 104 is applied to the AND gate 106 as well, however, passing each other, the output signal of the delay circuit 102 disappears, whereby the logical conditions are not established, so that the output signal, i.e. the shutter release command cannot be outputted to the AND gate 106.

However, when the push button switch 65b is pushed in again while the monostable multi-vibrator 104 is producing an output of "H" level after the finger is removed from the push button switch 65b, a voltage of "H" level is applied simultaneously to two input terminals of the AND gate 106 whereby, an output signal is produced as the shutter release command in the AND gate 106, In this case, signals in a state similar to the AND gate 106 are applied to respective input terminals in the OR gate 108, whereby the logical conditions are established, so that an output signal, i.e. the image standstill command SH can be produced. In consequence, the shutter of the camera 62 can be operated with the image displayed on the screen of the monitor television set 14b, being made stand still.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope comprising:
   an insertion section provided in the forward end thereof with a solid state imaging device;
   a manual control section connected to said insertion section, for performing various operations for observation;
   a display unit for monitor-displaying an object to be observed in response to a video signal from said solid state imaging device in the forward end of said insertion section;
   a single push button switch provided on said manual control section, being operated both at the time for making a displayed image stand still in said display unit and at the time for operating a shutter of a camera for photographing said displayed image; and
   a command producing circuit for producing an image standstill command to make a displayed image stand still in response to a first operation of said push button switch and for producing a command to release said shutter of the camera in response to a subsequent operation of said switch in the state where the former command is produced.

2. An endoscope as set forth in claim 1, wherein:
   said command producing circuit comprises a comparison voltage supply circuit for outputting comparison voltages of two types V1 and V3 ($V1>V3$), which are different in voltage level, a reference voltage producing circuit for changing the voltage level of a reference voltage V2 from a state of $V2>V1$ to a state of $V2<V3$, a first comparator for comparing the comparison voltage V1 with the reference voltage V2 to output an image standstill command when V1>V2, and a second comparator for comparing the comparison voltage V3 with the reference voltage V2 to output a shutter release command when V3>V2; and said reference voltage producing circuit includes said push button switch and the reference voltage is changed by the push operation of said push button switch.

3. An endoscope as set forth in claim 1, wherein said command producing circuit comprises:

a delay circuit for outputting pulse signals in a predetermined time duration in response to an operation of said push button switch;

a monostable multi-vibrator for outputting pulse signals having a predetermined pulse width in response to an output signal from said delay circuit;

an AND gate for taking an "AND" of outputs signals from said monostable multi-vibrator and said delay circuit to output a shutter release command; and an OR gate for taking an "OR" of output signals from said monostable multi-vibrator and said delay circuit to output an image standstill command.

* * * * *